Figure 1:
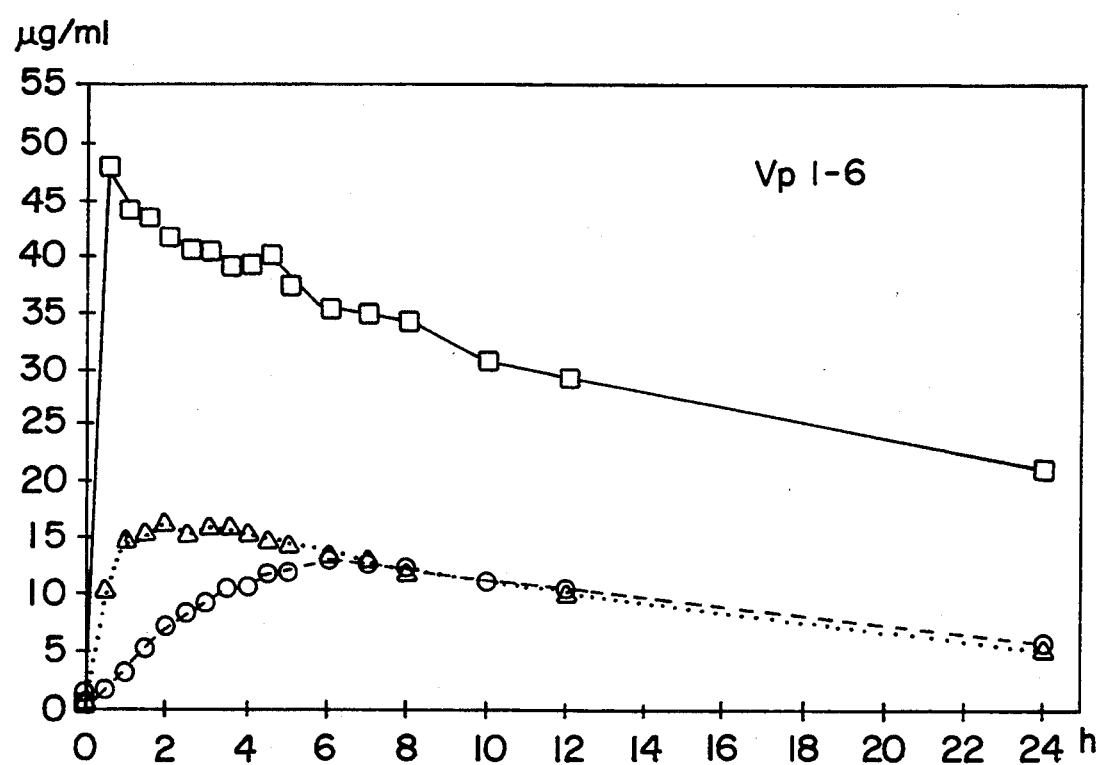

United States Patent [19]

Bertholdt et al.

[11] Patent Number: 5,419,915
[45] Date of Patent: May 30, 1995

[54] MEDICAMENT WITH AN ANALGESIC, ANTIPYRETIC AND/OR ANTIPHLOGISTIC ACTION AND USE OF 2-ETHOXYBENZOIC ACID

[75] Inventors: Heinz Bertholdt, Memmelsdorf; Dieter Michalczyk, Drosendorf; Rudolf Härtl, Hallstadt; Herbert Lieb, Bamberg, all of Germany

[73] Assignee: R. Pfleger Chemische Fabrik GmbH, Hallstadt, Germany

[21] Appl. No.: 848,852

[22] Filed: Mar. 10, 1992

[30] Foreign Application Priority Data

Apr. 18, 1991 [EP] European Pat. Off. .......... 91106203

[51] Int. Cl.$^6$ .............................................. A61K 9/48
[52] U.S. Cl. ..................... 424/451; 424/435; 424/489; 424/464
[58] Field of Search ............ 424/451, 435, 489; 514/870, 906; 562/435; 560/45

[56] References Cited

U.S. PATENT DOCUMENTS

| | | | |
|---|---|---|---|
| 3,681,445 | 8/1922 | Ruyle | 514/870 |
| 3,859,338 | 1/1975 | Engel | 562/435 |
| 3,953,496 | 4/1976 | Mori et al. | 560/45 |
| 4,055,574 | 10/1977 | Ackrell | 514/906 |
| 4,672,066 | 6/1987 | Carson et al. | 514/256 |

Primary Examiner—Thurman K. Page
Assistant Examiner—William E. Benston, Jr.
Attorney, Agent, or Firm—Anderson Kill Olick & Oshinsky

[57] ABSTRACT

The present invention relates to a medicament with an analgesic, antipyretic and/or antiphlogistic action based on a salicylic acid derivative. The prior art has constantly sought alternatives for active components such as acetyl salicylic acid (ASS) and ethenzamide in order to prevent incompatibility, or provide simpler and better, rapidly acting substances in the most varied administration forms. The invention has surprisingly proved that ethenzamide is very rapidly and completely metabolized in the human body to 2-ethoxybenzoic acid. Ethenzamide is only a pro-drug. A metabolization to salicylamide was exluded. It was also possible to prove the analgesic action of 2-ethoxybenzoic acid. It is correlated with the serum levels and is maintained for longer than 8 hours. 2-ethoxybenzoic acid is very rapidly resorbed. The serum maxima were reached after only 30 minutes and 2-ethoxybenzoic acid can still be detected in the serum after 24 hours. These characteristics make 2-ethoxybenzoic acid an ideal analgesic with a rapid action, which has no influence on blood clotting. The single doses can be reduced due to the higher bioavailability. Due to the physicochemical characteristics of 2-ethoxybenzoic acid the use in the form of a solution is possible, so that besides solid medicament forms for oral and rectal administration, it is also possible to prepare and use liquid formulations, such as dropping or injection solutions.

6 Claims, 2 Drawing Sheets

□——□ after oral administration of 500mg of 2-ethoxybenzoic acid

△····△ after oral administration of 500 mg of ethenzamide

○---○ after rectal administration of 500 mg of ethenzamide

□—□ after oral administration of 500 mg of 2-ethoxybenzoic acid

△····△ after oral administration of 500 mg of ethenzamide

○---○ after rectal administration of 500 mg of ethenzamide

MEDICAMENT WITH AN ANALGESIC, ANTIPYRETIC AND/OR ANTIPHLOGISTIC ACTION AND USE OF 2-ETHOXYBENZOIC ACID

The analgesic, antipyretic and antiphlogistic action of ethenzamide (2-ethoxybenzamide) has been known for several decades (cf. e.g. British patent 656 746). Ethenzamide is the amide of salicylic acid ethyl ether. As the derivative thereof it belongs to the group of non-steroidal antirheumatics (NSAR). It is at least equivalent to acetyl salicylic acid (ASS) with respect to its analgesic power. It is often used when other analgesics, such as e.g. ASS, lead to incompatibility reactions or exacerbate existing bleeding tendencies. The difficulties encountered by patients in ingesting ASS tablets have long been known (cf. German patent 963 270 and 30 00 743). Therefore drug research has always been interested in finding other alternatives for ASS. Numerous different preparation processes for ethenzamide are also known (cf. Beilstein's Handbuch der organischen Chemie, 4th edition, Springer-Verlag, 1983, E IVC, p. 175). Ethenzamide was introduced on the market e.g. in Germany in 1925, in France in 1942 and in Japan in 1954 and is used in more than 15 countries throughout the world. Between 1985 and 1989 world consumption was between 220 and 250 t/year, excluding China and the eastern bloc. In the case of 0.25 g/dose this represents an annual consumption of approximately 1 billion dosage units. The toxicology and pharmacology of ethenzamide are well documented, whereas the documentation of the clinical activity is based on a few studies carried out many years ago and generally performed with combination preparations.

Unlike in the case of salicylic acid, in ethenzamide the two reactive groups (phenolic OH-group and acid COOH-group) are blocked. As a result the chemical and physiological reactivity of the substance is modified compared with salicylic acid. It therefore becomes an ideal component for analgesic combination preparations.

As in the case of many long-known, proven pharmaceuticals, with respect to ethenzamide there are no well-founded details regarding the pharmacokinetics and metabolisms in humans. As a result of its very limited solubility in water ethenzamide is administered orally in tablet form or rectally as a suppository. There is no parenteral administration in the form of an injection solution or any solution for oral administration, so as to ensure a rapid action.

The problem of the invention is to make available an alternative medicament or drug, so as to avoid the aforementioned disadvantages.

This problem is solved by the medicament characterized in claim 1, namely by 2-ethoxybenzoic acid or its salts, or by the use according to claim 8.

The invention shows for the first time that the analgesically active ethenzamide only has a pro-drug function. The active principle is in fact its metabolite, namely 2-ethoxybenzoic acid, whose analgesic power has not as yet been recognized and can now be used in a direct, therapeutically advantageous manner.

The Expert is naturally aware of the fact that acid amides can be saponified in the presence of alkalis or acids in much the same way as esters with water. In spite of this fact being known for decades, neither the literature nor practical experience provides any information regarding the medical use of 2-ethoxybenzoic acid.

In fact, published research results serve no useful function, because they do not attribute any clinical significance to ethoxybenzoic acid (cf. J. Pharmacol. Exptl. Therap. vol.136, p.230, right-hand column, 1962, J.-P. Dupin et al in II Farmaco, 41 (31), 1986, Table I (Product VI) and P. Formijne in Koninkl. Med. Akad. Wetenschap, Proc., Ser.C 58, 1955, p. 576).

Surprisingly pharmacokinetic research has revealed that after resorption ethenzamide is completely and exclusively metabolized to 2-ethoxybenzoic acid, whose $C_{max}$ in the case of peroral administration is reached after 2 hours.

Pharmacodynamic research has proved for the first time that 2-ethoxybenzoic acid is analgesically active and can be used as a medicament.

The invention has shown that also following rectal administration ethenzamide is metabolized in the same way to 2-ethoxybenzoic acid. As expected, the maximum blood concentration is reached later, i.e. after about 6 hours. However, at the end of the resorption phase, the further course of the serum concentration curves is the same. Therefore the invention shows that the pharmacodynamic characteristics of ethenzamide are in reality based on its metabolite, i.e. 2-ethoxybenzoic acid which, unlike the difficultly water-soluble ethenzamide, has as a salt a good water-solubility and can therefore be used with advantage for the preparation of dropping or injection solutions.

Further advantages and features can be gathered from the subclaims, which can acquire inventive significance in conjunction with the main claim.

The invention is explained relative to bioavailability studies hereinafter and with reference to the attached drawings, wherein show:

FIG. 1 The 2-ethoxybenzoic acid plasma level over a 24 hour period following oral administration compared with ethenzamide after oral or rectal administration.

Figure 2:
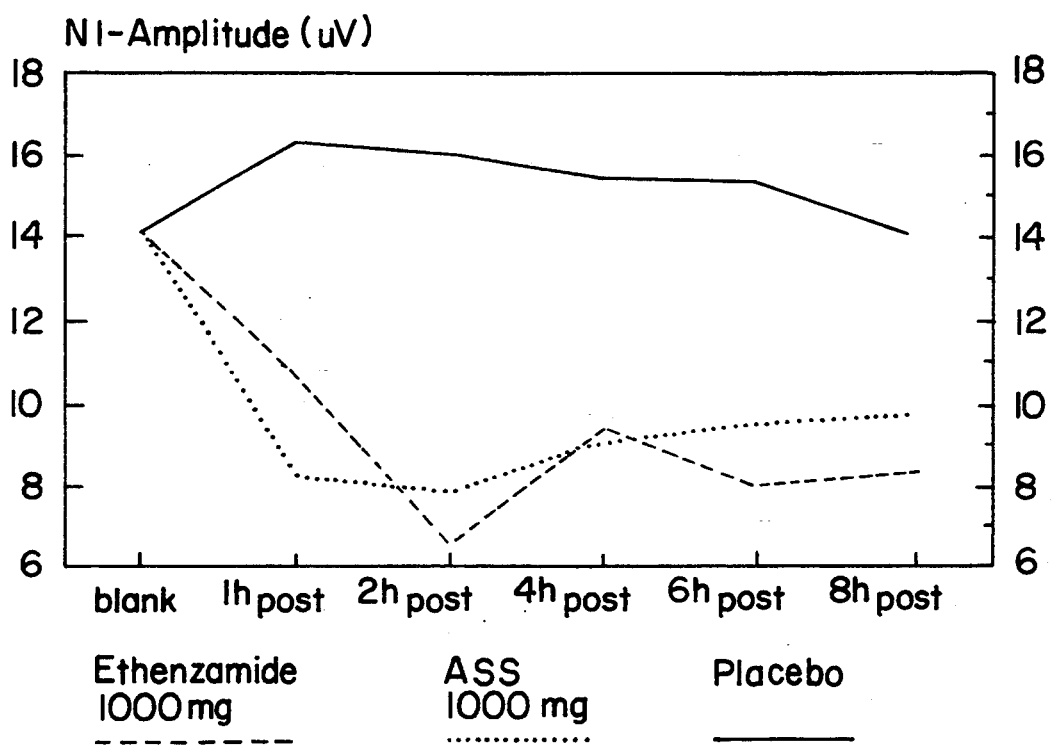

FIG. 2 The N1 amplitude of the laser SEP's for ethenzamide, ASS and placebo administration.

Figure 3:
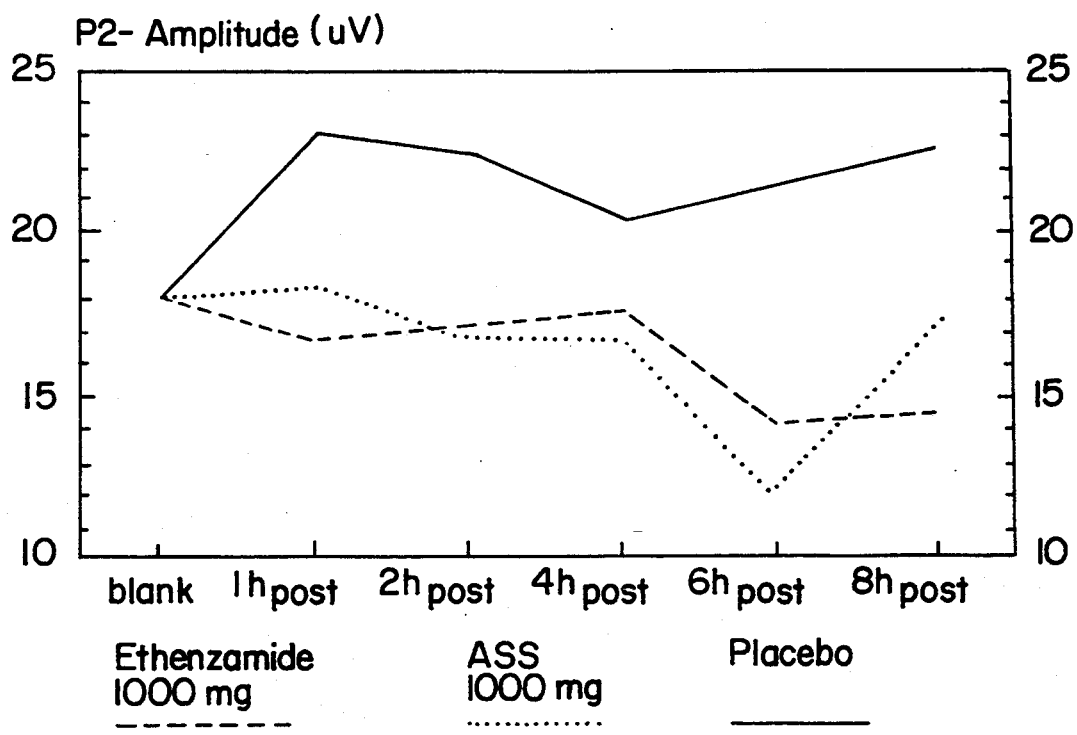

FIG. 3 A representation of the P2 amplitude of the laser SEP's for ethenzamide, ASS and placebo administration.

Following the oral administration of a 2-ethoxybenzoic acid solution (500 mg), the plasma levels over the entire research period are higher by a factor of 3 than the corresponding level following oral or rectal administration of ethenzamide preparations (tablets and suppositories in each case containing 500 mg of ethenzamide). Resorption takes place rapidly, the maxima being reached after only 30 minutes. However, the serum concentration is in parallel to that following the oral or rectal administration of ethenzamide. As a result of the faster resorption of the free acid and its 3 times higher bioavailability compared with the 2-ethoxybenzoic acid formed from ethenzamide, for the same activity the dosage can be considerably reduced. As salicylamide could not be detected in the serum, it is possible to refute the hitherto held opinion that salicylamide is the main metabolite of ethenzamide (cf. FIG. 1).

Simultaneously with the pharmacokinetic research, the analgesic power of ethenzamide was determined in comparison with ASS. Laser-caused somatosensory potentials under vigilance control were used for proving analgesia. This method also made it possible to prove peripheral (N-1) and central (P2) analgesic actions, which are statistically significant to the 0.1 level compared with placebo and were comparable with those of ASS. Action maxima were reached after 1 to 2 hours and were maintained up to the end of the measurement period (8 hours). The analgesic action is correlated with the serum levels of 2-ethoxybenzoic acid. The long-lasting response of the action (>8 h) was also noteworthy when measuring the central component (cf. FIGS. 2 and 3).

It was possible to prove by further research that, in the presence of acetyl salicylic acid, ethenzamide as the pro-drug or 2-ethoxybenzoic acid, has no inhibiting action on thrombocyte aggregation.

Hereinafter formulations are given for the inventive medicament preparations containing the active substance 2-ethoxybenzoic acid. It is clear that modifications to this formulation are possible within standard ranges without leaving the scope of the present invention.

The aqueous solutions were prepared in syrup form or as a dropping solution using salts of 2-ethoxybenzoic acid (EBS), sweeteners, (e.g. sorbitol solution, glycerol, sugar syrup, malt extract, saccharin/cyclamate), preservatives (e.g. parabene, ethanol), taste correcting agents, (e.g. raspberry, banana and malt flavours) and water.

EXAMPLE 1

Administration form: Syrup (250 mg EBS/5 ml) 5.66 g EBS sodium salt, 50.00 g sugar syrup, 0.18 g methyl p-hydroxybenzoate, 0.02 g propyl p-hydroxybenzoate, 2.00 g artificial raspberry flavour, 42.14 g water.

EXAMPLE 2

Administration form: Dropping solution (250 mg EBS/2 ml) 28.31 g EBS sodium salt, 5.00 g glycerol, 20.00 g ethanol, 2.00 g artificial raspberry flavour, 44.69 g water.

The injection solutions were prepared using salts of 2-ethoxybenzoic acid and water. Using dilute hydrochloric acid, the solution obtained was adjusted to pH 6.8 to 7.2, was filtered in particle-free form, ampouled and sterilized.

EXAMPLE 3

Administration form: Injection solution (500 mg/5 ml) 11.32 g EBS sodium salt Dilute hydrochloric acid to pH 6.8 to 7.2 ad 100.0 ml of water for injection purposes.

Solid formulations such as capsules and tablets were produced in per se known manner, in that an EBS salt was mixed with a filler (e.g. starch, lactose, cellulose, dicalcium phosphate), granulated in per se known manner with a suitable granulating aid (e.g. gelatin, polyvinyl pyrrolidone, soluble starch, soluble cellulose derivatives) and the granular material was introduced either into hard gelatin capsules or, following the addition of a lubricant (e.g. higher fatty acids and their alkaline earth metal salts, polyglycol, paraffin) was tabletted in per se known manner.

EXAMPLE 4

Administration Form: Capsule (250 mg EBS/capsule) 283.07 g of EBS sodium salt, 120.00 g of corn starch and 40.00 g of lactose are mixed together, granulated with an aqueous solution of 12.00 g soluble starch and with the dried granular material were mixed 2.00 g of magnesium stearate (=capsule filling material). For each individual capsule 457 mg of capsule filling material corresponding to 250 mg of EBS are dosed.

EXAMPLE 5

Administration form: Tablets (250 mg EBS/tablet) 283.07 g of EBS sodium salt, 150.00 g corn starch, 89.93 g lactose and 80.00 g cellulose powder are mixed together, granulated with a solution of 18.00 g of collidon 25 in 40 ml of water. After adding 25.00 g of cross-linked PVP and 4.00 g of magnesium stearate, the dried granular material is mixed and shaped into tablets weighing 650 mg.

Suppositories are produced in per se known manner using EBS and solid fat.

EXAMPLE 6

Administration form: Suppositories (250 mg EBS/suppository).

12.5 mg of EBS are dissolved in the melt at 40° to 450° C. of 87.5 g of solid fat and introduced in per se known manner into 2 g suppository forms.

We claim:

1. Medicament having the properties selected from the group consisting of analgesic, antipyretic and antiphlogistic action based on a salicylic acid derivative, comprising 1 to 500 mg of 2-ethoxybenzoic acid or its sodium, calcium or potassium salts, the medicament being produced in a form selected from the group consisting of orally administrable formulations, capsules, tablets, granulates, and powders.

2. Medicament according to claim 1, comprising that it is produced in the form of dropping and injection solutions.

3. Medicament according to claim 1, comprising that it incorporates pharmaceutical carriers, diluents and adjuvants.

4. Medicament according to claim 1 in solid form, comprising 250 mg of 2-ethoxybenzoic acid in the form selected from the group consisting of capsule, tablet and suppository.

5. Medicament according to claim 1 in liquid form, comprising 100 to 125 mg of 2-ethoxybenzoic acid/ml.

6. A method of producing an analgesic, antipyretic, antiphlogistic, or a combination thereof medicament formulation which comprises adding to the formulation from 1 to 500 mg of 2 ethoxybenzoic acid or its sodium, calcium or potassium salts.

* * * * *